United States Patent [19]
Kim

[11] Patent Number: 5,707,384
[45] Date of Patent: Jan. 13, 1998

[54] LANCET DEVICE FOR OBTAINING BLOOD SAMPLES

[75] Inventor: Inhwan Kim, Seongnam, Rep. of Korea

[73] Assignee: Teramecs Co., Ltd., Osaka, Japan

[21] Appl. No.: 660,600

[22] Filed: Jun. 11, 1996

[30] Foreign Application Priority Data

Jun. 26, 1995 [KR] Rep. of Korea ............... 1995-15318

[51] Int. Cl.$^6$ ............................................ A61B 17/14
[52] U.S. Cl. ................................. 606/181; 606/189
[58] Field of Search ............................. 606/181, 182, 606/189, 188, 184

[56] References Cited

U.S. PATENT DOCUMENTS

| | | | |
|---|---|---|---|
| 4,994,068 | 2/1991 | Hufnagle | 606/181 |
| 5,439,473 | 8/1995 | Jorgensen | 606/182 |
| 5,454,828 | 10/1995 | Schrage | 606/181 |
| 5,464,418 | 11/1995 | Schraga | 606/182 |
| 5,487,748 | 1/1996 | Marshall et al. | 606/181 |

*Primary Examiner*—Michael Buiz
*Assistant Examiner*—Kevin Truong
*Attorney, Agent, or Firm*—Darby & Darby

[57] ABSTRACT

A lancet device for obtaining blood samples comprising a body, a spring housed therein, a needle urged by the spring, a retaining mechanism for preventing the needle from projecting, a release part for releasing the retainment of the needle, and a needle cover covering the needle, wherein the retaining mechanism includes a needle-mounting member with an elastic member fixed thereto and a retaining part formed on the body and engaged with the elastic member, and the release part is a releasing member formed on the body.

9 Claims, 2 Drawing Sheets

LANCET DEVICE FOR OBTAINING BLOOD SAMPLES

BACKGROUND OF THE INVENTION

1. Field of the Invention

The present invention relates to a lancet device for obtaining blood samples.

2. Prior Art

The lancet device is an instrument used for obtaining a small amount of blood samples from fingertips or earlobes of testees for a simple blood test, etc. Such operation for obtaining blood samples when fulfilled by doctors or nurses as usual has no particular problems. Recently, patients such as diabetics need to take blood samples by themselves for self-management of the disease. In this case, a usual sewing needle or the like may be used for taking blood samples, but it is difficult or impossible for the patients, particularly, women or the aged, by themselves to cause the needle to pierce.

In this regard, there have been proposed lancet devices for obtaining blood samples which comprise a simple device with a needle adapted to protrude from the device in such a manner that the device is first abutted against the earlobe, etc., and then a rear part of the device is pushed or a lever or a button provided on a lateral side of the device is pushed, so that the needle is protruded to slightly pierce the skin and cause a quite small amount of bleeding.

In the rear part-push type among the conventional simple lancet devices, it is difficult for users to hold the device and push the rear part with one hand, and also difficult to apply force. The lateral lever or button-push type is operable with ease but needs to be changed in holding positions to keep the lever or button at an unvarying position with respect to user's hand.

In the conventional lancet devices, the needle is urged by a spring and engaged and retained by a retaining part formed on the device's body (surrounding the needle). The retaining part is removed or shifted to release the engagement of the needle with the body. For the purpose, force is to be applied in the direction as radially outwardly of the device's body. The action for applying the force in this manner is quite unreasonable and further needs use of a lever or a gear mechanism when the action is to be made only by pushing operation, resulting in complication in the force-applying action and the mechanism of the device.

Furthermore, the lancet devices in a disposable type have prevailed in recent years for prevention of infection with various bacteria and virus even when the blood-sample taking operation is fulfilled by doctors or nurses. The conventional lancet devices in the disposable type cannot be judged at a glance whether it has been used or not, i.e., to be identified as a new one, leading to waste in use of the devices.

SUMMARY OF THE INVENTION

An object of the present invention is to provide a lancet device for obtaining blood samples which enables that obtaining blood samples can be surely performed with a simple instrument and operation, having no fear or mistake that an old or used device is applied inadvertently.

DETAILED DESCRIPTION OF THE INVENTION

Figure 1:
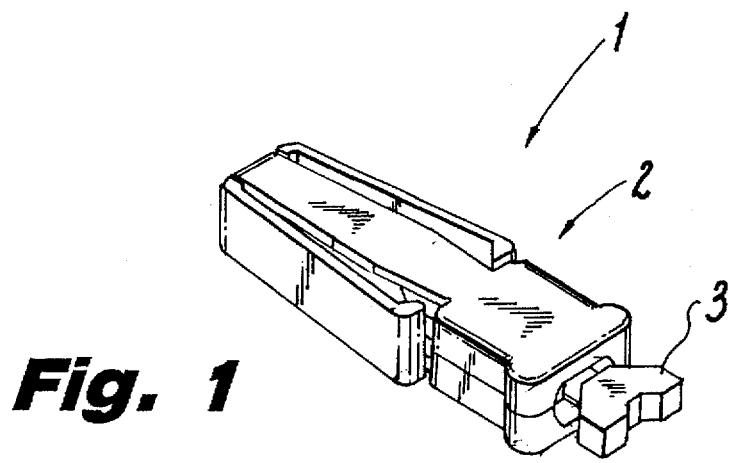
FIG. 1 is a perspective view illustrating an example of the lancet device for obtaining blood samples according to the present invention.

Under the above circumstances the inventor zealously studied and achieved the lancet device for obtaining blood samples according to the present invention. The lancet device for obtaining blood samples comprises a body, a spring housed therein, a needle urged by the spring, a retaining mechanism for preventing the needle from projecting, a release part for releasing the retainment of the needle, and a needle cover covering the needle, wherein the retaining mechanism includes a needle-mounting member with an elastic member fixed thereto and a retaining part formed on the body and engaged with the elastic member, and the release part includes a releasing member formed on the body.

The body referred to herein is the whole of a casing housing the needle and spring therein. The casing consists of two or more sections which can be divided or opened and closed and house therein the needle and spring. The body is provided with the releasing member which is shiftable and the retaining part which is engaged with a component including the needle to prevent the needle from projecting from the body.

The spring is provided for causing the needle to project from the body for bleeding and may be spiral as usual or folded or a leaf spring, which is stretchable when released from a shrinked state. The spring may be made of metal or plastics. In addition, the needle may use an ordinary needle which is usable in taking blood samples.

The retaining mechanism is provided for preventing, against the biasing force of the spring, the needle from projecting from the body and comprises, in the present invention, an elastic member fixed a member mounting the needle, and a regaining part formed on the body engageable with the elastic member. The member mounting the needle is made of plastics molded containing therein the needle, and the elastic member is adhered or melted to or integrally molded with the needle-mounting member. The elastic member is decreased in an engagement width by an exerted force from the outside so as to be released of engagement with the retaining part. In detail, the elastic member may be simply formed in a U-like shape which can be made smaller in the interval between the opposite portions by a pushing force exerted from both sides. The elastic member may be formed in a triangular or other shapes and also may have a stepped portion at the engaging part for sure engagement.

The retaining part which is formed on the body and engaged with the elastic member projects inwardly of the body. The elastic member when it is free abuts against the retaining part to thereby be prevented from further projecting.

The release member may use any features that make smaller the engagement width of the elastic member and is not limited of shapes, materials, etc., to any particular ones. The release member may employ a protuberance formed on the body, so that the body is pushed to cause the protuberance to push the elastic member. Alternatively, the lateral side of the body itself in place of the protuberance may be used to push the elastic member, the lateral side of the body serving as the release member. Furthermore, a separate button or the like for releasing the engagement of the elastic member may be provided on the laterial side of the body.

The needle cover covers the end of the needle and is removed in use of the device. The needle cover may be preferably integrally molded with the needle-mounting member and made smaller in thickness or diameter at a part at which the needle cover is cut or separated from the needle-mounting member by use of a relatively small force. In this feature, the needle cover is not separated from the needle-mounting member during a usual transportation, packaging or other operations, but can be removed by user's twisting or drawing the needle cover. The needle cover may be preferably provided at the free end with a small head for readily twisting off the cover.

EMBODIMENTS

Figure 2:
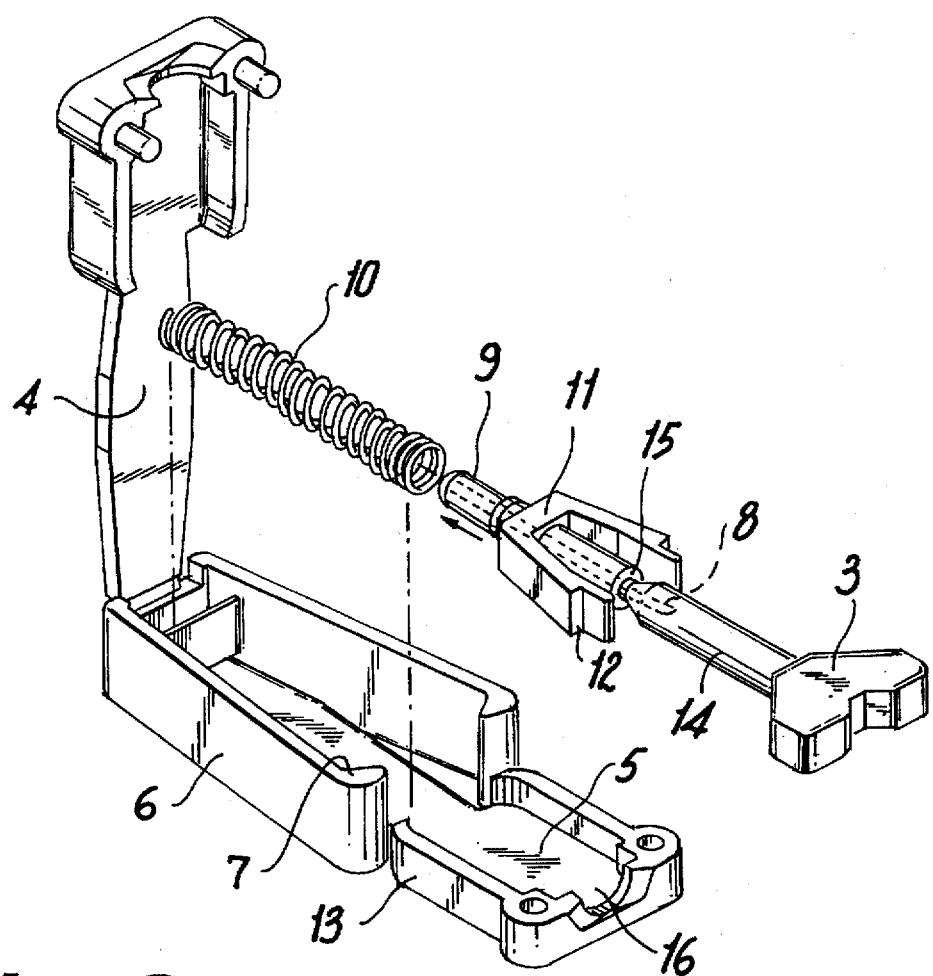
FIG. 2 is an exploded perspective view illustrating the example shown in FIG. 1, FIGS. 3a–c are sectional views illustrating a method of use of the example shown in FIG. 1.

Next, the present invention will be detailed with referring to the examples shown in the attached drawings. FIG. 1 is a perspective view showing an example of the lancet device for obtaining blood samples according to the present invention. In the drawing, the body 2 and the head 3 of the needle cover are seen. The lancet device is in the size of about 1 cm×4 cm. FIG. 2 is an exploded perspective view of the example shown in FIG. 1. An upper part 4 of the body 2 can be opened like a lid. Both lateral sides 6 of a lower part 5 of the body 2 are shiftable inwardly of the body, i.e., a bottom plate of the lower part 5 is partially cut to allow the lateral sides 6 to be moved in the space. The lateral sides 6 have protuberances 7 on the inner surfaces. A member 9 mounting or containing a needle 8 therein and a spring 10 for causing the needle 8 to project outwardly are housed in the body 2. An elastic member 11 is firmly fixed to (or may be integrally molded with) the needle-mounting member 9. The elastic member 11 has a stepped portion 12 at both sides to be abutted against and engaged with a retaining part 13 of the body 2. A needle cover 14 for protecting an end of the needle 8 is molded integrally with the needle-mounting member 9. A part 15 of the needle cover 14 at which the cover 14 is cut and removed to expose the needle 8 is made smaller in thickness or diameter to be readily cut. The needle cover 14 has at the free end a head 3 for readily twisting off the needle cover 14. The needle cover 14 projects outwardly from the body 2 through an opening 16.

Figure 3A:
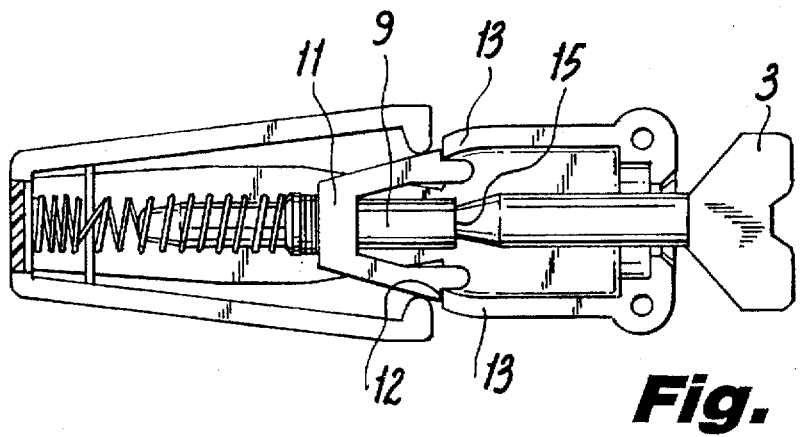
Figure 3B:
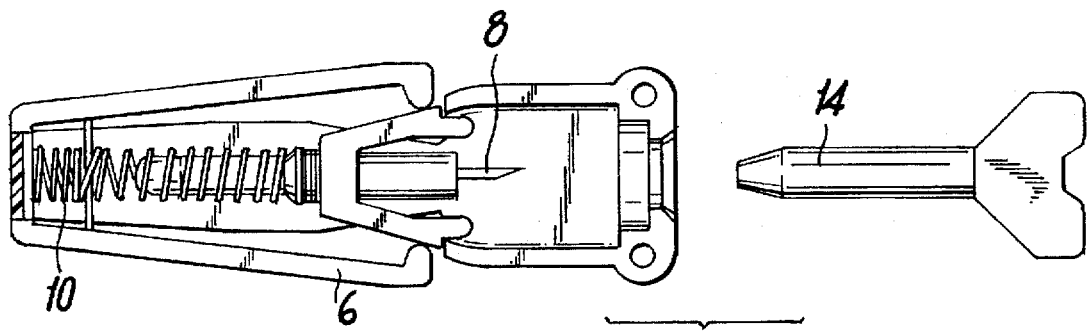
Figure 3C:
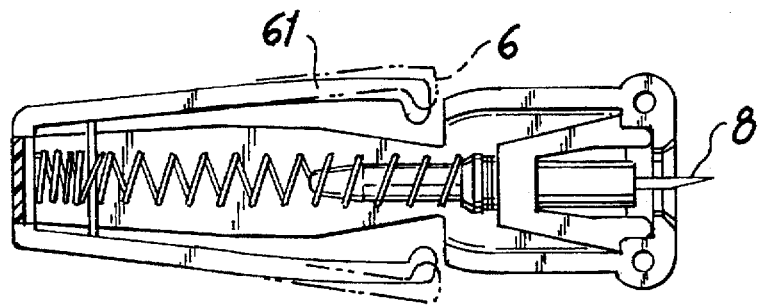

Next, specific operation of this example will be referred to. FIGS. 3(a)–(c) are sectional views illustrating the states of use of the example. FIG. 3(a) shows the state before use of the device, wherein the needle 8 is placed inside the needle cover 14 to be free of danger and fear of contact with bacteria and virus. In this state, the spring 10 is contracted and not expanded due to abutment between the stepped portion 12 and the retaining part 13.

The head 3 is twisted to twist off and remove the needle cover 14 at the part 15 from the needle-mounting member 9 (FIG. 3(b)). In this state, the needle 8 is exposed in the body 2 to thereby be not contacted with the user's hands.

Next, the device is brought, at the opening 16, into abutment against any locations for taking blood samples, for example, users' hands, earlobes, etc., and both sides of the body 2 are pinched to push the lateral sides 6 (FIG. 3(c)) to shift them to the position indicated by the lateral sides 61. The protuberances 7 on the lateral sides push both of the opposite portions of the elastic member 11 to make smaller an interval between the corresponding stepped portions 12 than an interval between the corresponding side walls of the retaining part 13, thereby releasing engagement between the elastic member 11 and the retaining part 13. In this instance, the needle 8 is projected from the body through the opening 16 by the force of spring. An interval from a plane including the opening 16 abutting against the testee's skin to the utmost end of the needle 8 is the piercing amount or depth of the needle 8. Naturally, the needle 8 does not stop at an utmost position in projecting but retracts immediately to finally stop at a position where the spring does neither expand nor contract. The spring is preferably adjusted to allow the free end of the needle 8 to be located in the body at that final stoppage position of the needle 8.

In this example, a stopper for preventing the needle from excessively projecting is provided around the opening 16 of the body 2 to be engageable with the stepped portions 12, so that the elastic member 11 is stopped at the stopper to ensure safety.

EFFECT OF THE INVENTION

The present invention explained above has the following effects.
(1) The needle before use is completely covered, so that the needle has no fear of contact with bacteria or virus.
(2) The needle is projected only by pushing the lateral sides of the body, requiring a simple operation and a small amount of force. But, there is no fear of unexpected projection of the needle since the device needs to be pushed at both lateral sides.
(3) The device needs only to be made smaller in an interval of the opposite portions of the housed elastic member, so that the device is operated by a simple action and needs a simple structure.
(4) Most of the structure of the device can be built up by integral molding of plastics to be not expensive to produce and the device can be sold at a price fully reasonable as disposable type.

What we claimed is:

1. A lancet device for obtaining blood samples comprising:
   (1) a body having upper and lower parts, two lateral sides and two lateral retaining parts;
   (2) a spring housed in said body;
   (3) a needle in a mounting member and being urged by said spring; and
   (4) an elastic member fixed to said mounting member and engaging said lateral retaining parts to prevent said needle from being projected;
   wherein each said lateral side comprises a trigger element which inwardly deforms said elastic member when depressed by the user, and said elastic member is disengaged from said lateral retaining parts when all said trigger elements are depressed substantially simultaneously, thereby releasing said needle.

2. The lancet device of claim 1 further comprising a removable needle cover.

3. The lancet device of claim 2, wherein said needle cover has a head and is attached to said mounting member at a cut-point which may be easily severed to remove said needle cover from said needle.

4. A lancet device for obtaining blood samples as set forth in claim 1, wherein said lancet device is substantially symmetric.

5. A lancet device for obtaining blood samples as set forth in claim 1, wherein said elastic member has two arms and is substantially U-shaped, each said arm having a stepped portion.

6. A lancet device for obtaining blood samples as set forth in claim 1, wherein each said lateral side has inwardly projecting protuberances.

7. A lancet device for obtaining blood samples as set forth in claim 1, wherein said lower part, lateral sides, and lateral retaining parts of said body are integrally molded, and said upper part of said body is attached to said integrally molded form with a hinge and may be freely opened and closed.

8. A lancet device as set forth in claim 7, wherein said hinge comprises a protuberance on said upper part which engages a groove in said integrally molded form.

9. A lancet device as set forth in claim 7, wherein said hinge comprises a protuberance on said integrally molded form which engages a groove in said upper part.

* * * * *